(12) United States Patent
Ou et al.

(10) Patent No.: US 9,469,578 B2
(45) Date of Patent: Oct. 18, 2016

(54) ENERGY EFFICIENT PROCESSES FOR XYLENES PRODUCTION

(71) Applicant: ExxonMobil Chemical Patents Inc., Baytown, TX (US)

(72) Inventors: John D. Y. Ou, Houston, TX (US); Jeevan S. Abichandani, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 8 days.

(21) Appl. No.: 14/443,945

(22) PCT Filed: Nov. 21, 2013

(86) PCT No.: PCT/US2013/071181
§ 371 (c)(1),
(2) Date: May 19, 2015

(87) PCT Pub. No.: WO2014/085178
PCT Pub. Date: Jun. 5, 2014

(65) Prior Publication Data
US 2015/0299071 A1    Oct. 22, 2015

Related U.S. Application Data

(60) Provisional application No. 61/732,150, filed on Nov. 30, 2012.

(30) Foreign Application Priority Data

Jan. 23, 2013    (EP) ..................................... 13152289

(51) Int. Cl.
*C07C 5/27*    (2006.01)
*C10G 45/58*    (2006.01)

(52) U.S. Cl.
CPC ............. *C07C 5/2732* (2013.01); *C07C 5/277* (2013.01); *C07C 5/2729* (2013.01); *C10G 45/58* (2013.01)

(58) Field of Classification Search
CPC ....................................................... C07C 5/27
USPC ......................... 585/477, 478, 479, 300, 304
See application file for complete search history.

(56) References Cited

U.S. PATENT DOCUMENTS

| 6,180,550 B1 | 1/2001 | Beck et al. |
| 6,198,013 B1 | 3/2001 | Mohr et al. |
| 6,448,459 B1 | 9/2002 | Magne-Drisch et al. |
| 6,872,866 B1 | 3/2005 | Nemeth et al. |

(Continued)

FOREIGN PATENT DOCUMENTS

| WO | WO00/10944 | 3/2000 |
| WO | WO2007/127049 | 11/2007 |

(Continued)

OTHER PUBLICATIONS

U.S. Appl. No. 12/612,007, filed Nov. 4, 2009, Ou et al.

(Continued)

*Primary Examiner* — Thuan D Dang

(57) ABSTRACT

The invention is directed to a process to produce para-xylene and, optionally, ortho-xylene, including coupling two in-series xylenes separation systems with two parallel isomerization systems for energy savings and/or productivity increases.

13 Claims, 3 Drawing Sheets

(56) References Cited

U.S. PATENT DOCUMENTS

| | | |
|---|---|---|
| 6,878,855 B2 | 4/2005 | Deckman et al. |
| 7,179,367 B2 | 2/2007 | Feng et al. |
| 7,244,409 B2 | 7/2007 | Burgfels et al. |
| 7,368,620 B2 | 5/2008 | Zhou et al. |
| 7,371,913 B2 | 5/2008 | Bauer |
| 7,439,412 B2 | 10/2008 | Ou et al. |
| 7,495,137 B2 | 2/2009 | Zhou et al. |
| 7,553,998 B2 | 6/2009 | Bresler et al. |
| 7,592,499 B2 | 9/2009 | Wolff et al. |
| 7,626,065 B2 | 12/2009 | Ou et al. |
| 7,663,010 B2 | 2/2010 | Levin |
| 7,915,471 B2 | 3/2011 | Leflaive et al. |
| 7,932,426 B2 | 4/2011 | Bauer |
| 7,989,672 B2 | 8/2011 | Kinn et al. |
| 8,273,934 B2 | 9/2012 | Ou et al. |
| 8,344,197 B2 | 1/2013 | Lattner et al. |
| 8,439,412 B2 | 5/2013 | Klimek |
| 2007/0249882 A1 | 10/2007 | Ou |
| 2009/0149686 A1 | 6/2009 | Leflaive et al. |
| 2012/0108868 A1 | 5/2012 | Pilliod et al. |
| 2012/0330075 A1 | 12/2012 | Ou et al. |

FOREIGN PATENT DOCUMENTS

| | | |
|---|---|---|
| WO | WO2011/133326 | 10/2011 |
| WO | WO2012/058106 | 5/2012 |
| WO | WO2012/058108 | 5/2012 |

OTHER PUBLICATIONS

U.S. Appl. No. 61/326,445, filed Apr. 21, 2010, Ou et al.

Conventional PX and Optional OX Production Process

An Embodiment of the Present Invention

Another Embodiment of the Present Invention

ENERGY EFFICIENT PROCESSES FOR XYLENES PRODUCTION

CROSS-REFERENCE OF RELATED APPLICATIONS

This application is a National Stage Application of International Application No. PCT/US2013/071181, filed Nov. 21, 2013, which claims priority to and the benefit of Provisional Application No. 61/732,150, filed Nov. 30, 2012.

FIELD OF THE INVENTION

This invention relates to energy efficient processes for producing para-xylene and, optionally, ortho-xylene.

BACKGROUND OF THE INVENTION

Ethylbenzene (EB), para-xylene (PX), ortho-xylene (OX), and meta-xylene (MX) are often present together in $C_8$ aromatic streams from chemical plants and oil refineries. Although EB is an important raw material for the production of styrene, for a variety of reasons, most EB feedstocks used in styrene production are produced by alkylation of benzene with ethylene, rather than by recovery from a $C_8$ aromatics stream. Of the three xylene isomers, PX has the largest commercial market and is used primarily for manufacturing terephthalic acid and terephthalate esters for use in the production of various polymers such as poly(ethylene terephthalate), poly(propylene terephthalate), and poly (butene terephthalate). While OX and MX are useful as solvents and raw materials for making products such as phthalic anhydride and isophthalic acid, market demand for OX and MX and their downstream derivatives is much smaller than that for PX.

Given the higher demand for PX as compared with its other isomers, there is significant commercial interest in maximizing PX production from any given source of $C_8$ aromatic materials. However, there are two major technical challenges in achieving this goal of maximizing PX yield. Firstly, the $C_8$ aromatics are difficult to separate due to their similar chemical structures, physical properties, and identical molecular weights. Secondly, the four $C_8$ aromatic compounds, particularly the three xylene isomers, are usually present in concentrations dictated by the thermodynamic equilibriums of the $C_8$ aromatics. Under the conditions of 200° C. to 500° C. at which xylenes are processed in typical petrochemical plants, the thermodynamic equilibrium content calculated based on free energy of formation is often approximately 24 wt % PX, 56 wt % MX, and 20 wt % OX, based on the total amount of xylenes in the feed. Such a relatively low PX equilibrium concentration leads to large amounts of MX and OX recycles which are reprocessed through several energy intensive operations, making PX production a costly practice in terms of energy consumption and capital investments. Present demand for PX is fairly large and is expected to grow in the future. Consequently, a system maximizing PX production in an energy-efficient manner is highly sought after.

A typical xylenes production process is illustrated in FIG. 1. The feed streams to the system comprise $C_8^+$ aromatics and may come from one or more sources, including $C_8^+$ reformate 1 (see, for instance, U.S. Pat. No. 7,179,367), $C_8^+$ selective toluene disproportionation product 17 (see, for instance, U.S. Pat. No. 7,989,672), $C_8^+$ transalkylation product 2 (see, for instance, U.S. Pat. No. 7,663,010), $C_8^+$ toluene disproportionation product 15 (see, for instance, U.S. Pat. No. 6,198,013), and $C_8$ aromatics, produced from toluene and/or benzene methylation with methanol (see, for instance, U.S. Application 2011/0092755). These streams typically comprise $C_8$ and heavier aromatics which are processed along with a recycle stream 10 in one or more fractionators 16 for the removal $C_9^+$ aromatics (aromatic compounds having nine or more carbon atoms) and, optionally, OX in stream 3, which, optionally, can be subsequently separated in fractionator 14 into OX overhead 4 and $C_9^+$ bottoms 5. The $C_9^+$ aromatics could have adverse effects on downstream PX Recovery 12 and vapor-phase xylenes isomerization unit 13 if not removed from the feed stream(s) as bottoms by the aforementioned fractionation unit 16 and, optionally, 14.

The removal of $C_9^+$ aromatics and, optionally, OX in fractionator(s) 16 thus yields an overhead $C_8$ aromatics-rich stream 6 which typically contains PX at a concentration of below or near the thermodynamic equilibrium concentration. The $C_8$-aromatics-rich stream 6 is processed to selectively recover PX in a xylenes separation system shown as PX recovery 12 which may be one or both of selective adsorption or crystallization. A PX-rich product stream 7, typically having more than 99.7 wt % PX is recovered, and a PX-depleted raffinate stream 8 containing the balance of $C_8$ aromatics stream passes to vapor-phase xylenes isomerization 13. Usually, in the presence of hydrogen in stream 9, vapor-phase xylenes isomerization 13 generates an isomerate (i.e., isomerization product) stream 19 having near-equilibrium concentration of xylene isomers using one or more of a variety of catalysts which may also convert EB to benzene and ethane or may convert EB to near-equilibrium xylene isomers. The isomerate, or isomerization product stream 19 passes to detoluenization fractionation 18 which removes $C_7^-$ hydrocarbons (hydrocarbon compounds having seven or less carbon atoms) in stream 11 to yield isomerate recycle stream 10. Isomerate recycle stream 10 is processed in fractionator 16.

The above processing steps, including fractionator 16, PX recovery 12, vapor-phase xylenes isomerization 13, and detoluenization fractionation 18, are all energy-intensive operations. As shown in FIG. 1, conventional xylenes production processes normally involve recycling a stream between the separations, in which most of the PX is recovered and a PX-depleted raffinate stream is produced, and the isomerization, in which the PX content of the PX-depleted raffinate stream is returned back towards equilibrium concentration. However, these processes suffer from the deficiencies that (1) the low PX concentration in the feed to PX recovery 12 leads to the large quantity of recycle stream 10 and (2) recycle stream 10 must be reprocessed through all the energy-intensive steps. Such deficiencies make conventional xylenes production a costly operation in terms of both capital and energy.

Improving such energy-intensive processes is an active area of research, but it is not a simple matter of optimization of each individual step, as optimization of one step may negatively affect one or more steps in the overall system. Examples of proposed improvements include the following.

U.S. Pat. No. 7,439,412 discloses a process for recovering one or more high purity xylene isomers from a $C_8^+$-aromatic feed stream including the use of an isomerization unit under liquid-phase conditions. In an example, the product of the liquid-phase isomerization unit is returned to the first fractionation tower in the system.

U.S. Pat. No. 7,553,998 discloses a process for recovering one or more high-purity xylene isomers from a feed having substantial content of $C_9^+$ aromatic hydrocarbons comprising de-ethylation of heavy aromatics followed by fractionation and then passing the stream to a $C_8$-aromatic-isomer recovery to recover high-purity xylene isomers with lowered energy costs. Streams passing through an isomerization unit under liquid isomerization conditions are split, with a portion sent to an isomer recovery unit, and a portion is purged.

U.S. Pat. No. 7,626,065 discloses processes for recovering one or more high-purity xylene isomers from a feed having substantial content of $C_9^+$ aromatic hydrocarbons comprising using an additional xylenes separator to generate a PX-rich effluent stream, which serves as the feed to PX recovery, and a PX-depleted effluent stream, which is converted to near equilibrium using an additional xylenes isomerization. The arrangements save energy by reducing the amount of isomerate recycle.

WO 2012/058106 and WO 2012/058108 describe processes for producing a PX-rich product, such as (a) providing a PX-depleted raffinate stream; (b) providing a parallel configuration of vapor-phase and liquid-phase isomerization units; and (c) splitting the PX-depleted raffinate stream and isomerizing the two split streams in the two parallel isomerization units respectively. The process saves energy by reducing the amount of isomerate recycle from vapor-phase xylenes isomerization which is more energy intensive than liquid-phase xylenes isomerization.

WO 2011/133326 is directed to a xylenes isomerization process, including a liquid-phase isomerization, for the production of equilibrium or near-equilibrium xylenes, wherein the process conditions include a temperature of less than 295° C. and a pressure sufficient to maintain the xylenes in liquid phase that uses at most only ppm levels of hydrogen and that in embodiments can be regenerated numerous times by an in situ procedure.

Other references of interest include U.S. Publication Nos. 2008/0262282; 2009/0149686; 2009/0182182; U.S. Pat. Nos. 6,448,459; 6,872,866; and 7,368,620.

Present demand for PX is fairly large and is expected to grow in the future. Consequently, a system maximizing PX production in an energy-efficient manner is highly sought after. While prior attempts to improve PX and, optionally, OX production abound, most have not been able to reduce the xylenes recycle and circumvent the energy intensive vapor-phase isomerization unit simultaneously. The present inventors have surprisingly discovered processes which reduce xylenes recycle and avoid vapor-phase isomerization to further lower energy consumption by coupling two in-series xylenes separation systems with two parallel isomerization systems. The improved processes significantly reduce the energy required and/or increase the production capacity for producing high purity PX and, optionally, OX.

SUMMARY OF THE INVENTION

The invention is related to a process for producing a PX-rich product comprising: (1) separating a feedstock comprising $C_8^+$ aromatics to produce a $C_8$ aromatics-rich stream and a $C_9^+$ aromatics-rich stream; (2) separating at least a portion of said $C_8$ aromatics-rich stream to produce a PX-rich product stream and a PX-depleted raffinate stream; (3) isomerizing at least a portion of said PX-depleted raffinate stream to produce a first isomerate stream having a higher PX concentration than said PX-depleted raffinate stream; (4) isomerizing at least another portion of said PX-depleted raffinate stream to produce a second isomerate stream having a higher PX concentration than said PX-depleted raffinate stream; (5) separating $C_7^-$ hydrocarbons from at least a portion of said second isomerate stream and, optionally, at least a portion of said first isomerate stream to produce a $C_7^-$ hydrocarbons-rich stream and a $C_7^-$ hydrocarbons-depleted isomerate stream having a lower $C_7^-$ hydrocarbons concentration than said second and, optionally, said first isomerate streams; (6) separating at least a portion of said first isomerate stream and, optionally, at least a portion of said $C_7^-$ hydrocarbons-depleted isomerate stream to produce a PX-rich effluent stream and a PX-depleted effluent stream; (7) supplying a least a portion of said PX-depleted effluent stream to isomerizing step (3); (8) recycling at least a portion of said PX-rich effluent stream to separating step (1) and, optionally, separating step (2); and (9) recovering at least a portion of said PX-rich product streams as said PX-rich product. Optionally, the $C_9^+$-aromatics-rich stream may then be separated downstream of separating step (1), such as by fractionation, to produce an OX-rich steam and an OX-depleted $C_9^+$ stream.

The invention is also directed to a process for producing a PX-rich product comprising: (1) separating a feedstock comprising $C_8^+$ aromatics to produce a $C_8$ aromatics-rich stream and a $C_9^+$ aromatics-rich stream; (2) separating at least a portion of said $C_8$ aromatics-rich stream to produce a PX-rich effluent stream and a PX-depleted effluent stream; (3) separating said PX-rich effluent stream to produce a PX-rich product stream having a higher PX concentration than said PX-rich effluent stream and a PX-depleted raffinate stream; (4) isomerizing at least a portion of said PX-depleted effluent stream and at least a portion of said PX-depleted raffinate stream to produce a first isomerate stream having a higher PX concentration than said PX-depleted effluent and said PX-depleted raffinate streams; (5) isomerizing at least another portion of said PX-depleted raffinate stream to produce a second isomerate stream having a higher PX concentration than said PX-depleted raffinate streams; (6) separating $C_7^-$ hydrocarbons from at least a portion of said second isomerate stream and, optionally, at least a portion of said first isomerate stream to produce a $C_7^-$ hydrocarbons-rich stream and a $C_7^-$ hydrocarbons-depleted isomerate stream having a lower $C_7^-$ hydrocarbons concentration than said second and, optionally, said first isomerate streams; (7) recycling at least a portion of at least one of said first isomerate stream and said $C_7^-$ hydrocarbons-depleted isomerate stream to said separating step (1); and (8) recovering at least a portion of said PX-rich product stream as said PX-rich product. Optionally, the $C_9^+$-aromatics-rich stream may then be separated downstream of separating step (1), such as by fractionation, to produce an OX-rich steam and an OX-depleted $C_9^+$ stream.

BRIEF DESCRIPTION OF THE DRAWINGS

In the accompanying drawings, like reference numerals are used to denote like parts throughout the several views.

DETAILED DESCRIPTION OF THE INVENTION

Figure 1:
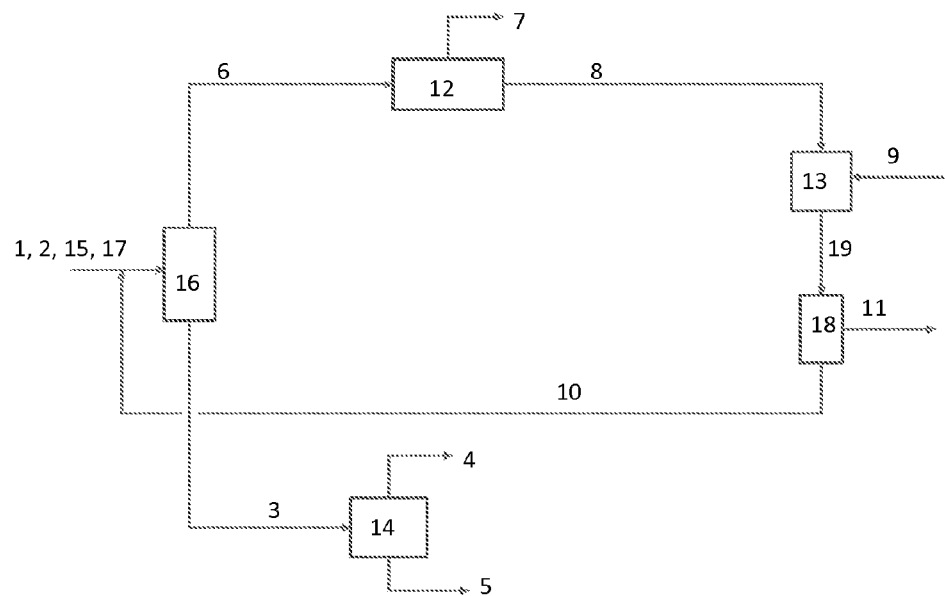
FIG. 1 is a schematic illustrating typical processing of $C_8^+$ aromatics to produce PX and optionally OX.

All patents, patent applications, test procedures, priority documents, articles, publications, manuals, and other documents cited herein are fully incorporated by reference to the extent such disclosure is not inconsistent with the present application and for all jurisdictions in which such incorporation is permitted.

When numerical lower limits and numerical upper limits are listed herein, ranges from any lower limit to any upper limit are contemplated.

One having ordinary skill in the art understands that the embodiments discussed in this application do not represent all the possible apparatus or process variations embodied by the present disclosure. In addition, many pieces of equipment and apparatus and certain processing steps may be needed for industrial, commercial or even experimental purposes. Examples of such equipments and apparatus and processing steps are, but not limited to, distillation columns, fractionation columns, heat exchanges, pumps, valves, pressure gauges, temperature gauges, liquid-vapor separators, feed and product driers and/or treaters, clay treaters, feed and/or product storage facilities, and processes and steps for process control. While such equipment, apparatus, and steps that are not needed for understanding the essence of the present application are not shown in the drawings, some of them may be mentioned from time to time to illustrate various aspects of the disclosure. It is also noted that some of the equipment may be placed at different places in the process depending on the conditions of the processes.

For the purposes of this invention and the claims thereto: "$C_8$ aromatics" shall mean aromatic compounds having eight carbon atoms, including ethylbenzene (EB), para-xylene (PX), meta-xylene (MX), and ortho-xylene (OX); "$C_8^+$ aromatics" shall mean aromatic compounds having eight or more carbon atoms, including EB, PX, MX, and OX; "$C_9^+$ aromatics" shall mean aromatic compounds having nine or more carbon atoms; "$C_7^-$ hydrocarbons" shall mean hydrocarbons having seven carbon atoms or less; "rich" shall mean that the concentration of a compound in a resulting stream is higher than the concentration of the compound in the starting stream from which the resulting stream is derived, for example, a PX-rich stream derived from a starting stream is one where the PX concentration based on the total amount of xylenes in the stream is higher than the PX concentration based on the total amount of xylenes in the starting stream; "depleted" shall mean that the concentration of a compound in a resulting stream is lower than the concentration of the compound in the starting stream from which the resulting stream is derived, for example, a PX-depleted stream derived from a starting stream is one where the PX concentration based on the total amount of xylenes in the stream is lower than the PX concentration based on the total amount of xylenes in the starting stream; "near-equilibrium concentration of xylene isomers" shall mean the concentration of PX based on the total amount of xylenes in the stream is within 85% to 100% of its equilibrium concentration while the concentrations of MX and OX vary to balance the composition, for example, if the xylene equilibrium concentrations are 24 wt % PX, 56 wt % MX, and 20 wt % OX at 350° C., then a stream having the xylene concentrations of 21 wt % PX, 58 wt % MX, and 21 wt % OX at 350° C. would be having a near-equilibrium concentration of xylene isomers.

The invention is related to the coupling of two essentially in-series xylenes separation systems with two parallel isomerization systems. (By essentially in-series is meant that the systems may be directly or indirectly linked, for example: 1) two separation systems that are directly linked have one separation system's product becoming the other's feed, or 2) two separation systems that are indirectly linked have other unit operations, such as distillation columns or isomerization reactors, in between the two separation systems.) The coupling significantly reduces the quantity of xylenes recycle and the energy required for recycle processing. The benefits of such improvements may be realized in several ways including saving energy at constant PX production, maximizing capacity to increase PX production, or both.

Feedstock

The feedstock employed in the present process may be any $C_8^+$ hydrocarbon feedstock containing $C_8$ aromatic hydrocarbons, such as a reformate stream, a hydrocracking product stream, a xylene or EB reaction product stream, an aromatic alkylation product stream, an aromatic disproportionation stream, an aromatic transalkylation stream, and/or a Cyclar™ process stream. The feedstock may further comprise recycle stream(s) from the isomerization step(s) and/or various separating steps. The $C_8^+$ hydrocarbon feedstock comprises PX, together with MX, OX, and/or EB. In addition to xylenes and EB, the $C_8^+$ hydrocarbon feedstock may also contain certain amounts of other aromatic or even non-aromatic compounds. Examples of such aromatic compounds are benzene, toluene, and $C_9^+$ aromatics such as mesitylene, pseudo-cumene, and others. These types of feed stream(s) are described in "Handbook of Petroleum Refining Processes," Eds. Robert A. Meyers, McGraw-Hill Book Company, Second Edition, all relevant parts of which are hereby incorporated by reference.

Process Description

The processes of the present application comprise an initial separating step that serves to remove $C_9^+$ hydrocarbons from a $C_8^+$ hydrocarbons feedstock to generate a stream rich in $C_8$ aromatics. Because of the differences in molecular weights, boiling points, and other physical and chemical properties, the $C_9^+$ hydrocarbon compounds, aromatic or non-aromatic, can be separated relatively easily from the xylenes and EB. Generally, therefore, the first separating step includes fractional distillation, although other separation methods, such as crystallization, adsorption, a reactive separation, a membrane separation, extraction, or any combination thereof, can also be used. These separation methods are described in "Perry's Chemical Engineers' Handbook," Eds. R. H. Perry, D. W. Green, and J. O. Maloney, McGraw-Hill Book Company, Sixth Edition, 1984, and "Handbook of Petroleum Refining Processes," Eds. Robert A. Meyers, McGraw-Hill Book Company, Second Edition, all relevant parts of which are hereby incorporated by reference.

After removal of the $C_9^+$ hydrocarbons, the present invention comprises two essentially in-series xylenes separating systems. One of the two systems serves to separate the resultant $C_8$ aromatics-rich stream(s) into a PX-rich effluent stream and a PX-depleted effluent stream. In one embodiment, the PX-rich effluent stream comprises at least 30 wt %, preferably at least 35 wt % PX, more preferably at least 40 wt % PX, based on the total weight of xylenes in the PX-rich effluent stream. The other xylenes separating system serves as PX recovery, which recovers a PX-rich product stream from the PX-rich effluent stream and, optionally, other $C_8$ aromatic streams. In one embodiment, the PX-rich product stream comprises at least 70 wt % PX, preferably at least 80 wt % PX, more preferably at least 90 wt % PX, even preferably at least 95 wt % PX, and most preferably at least 99 wt % PX, based on the total weight of the PX-rich product stream. Each of the xylenes separating systems may comprise at least one of a crystallization unit; an adsorption unit that uses either zeolitic adsorbents, such as a PAREX™ unit, or an ELUXYL™ unit or non-zeolitic adsorbents; a reactive separation unit; a membrane separation unit; an extraction unit; a distillation unit; a fractionation unit; or any combination thereof. Examples of these types of separation unit(s) and their designs are described in "Perry's Chemical Engineers' Handbook," Eds. R. H. Perry, D. W. Green, and J. O. Maloney, McGraw-Hill Book Company, Sixth Edition, 1984 and "Handbook of Petroleum Refining Processes," Eds. Robert A. Meyers, McGraw-Hill Book Company, Second Edition, all relevant parts of which are hereby incorporated by reference.

For the present disclosure, a xylenes separating system may be carried out in a liquid phase, a vapor (gas) phase, a super critical phase, or a combination thereof. The consumption of energy and the specific composition of the aromatic feed stream being separated determine the separating conditions and the physical state of the aromatic feed stream in the xylenes separator.

The processes of the present invention also comprise two parallel isomerization systems, in each of which a feed stream comprising $C_8$ aromatic compounds is isomerized to produce an isomerization effluent. The feed stream to each isomerization system comprises PX in a concentration below its equilibrium concentration relative to other interconvertible $C_8$ aromatic compounds under the isomerization conditions. Each catalyzed isomerization system serves to increase the PX concentration to near its equilibrium level. The isomerization step may also serve to convert part or all of EB present in the feed stream to benzene and light hydrocarbons (i.e., hydrocarbons having less than 6 carbons per molecule). Alternatively, the isomerization step may also serve to isomerize part or all of EB present in the feed stream to xylene(s).

There are many catalysts or combinations of catalysts that can be used in each isomerization system to effect the desired reaction(s). For vapor-phase isomerization, there are generally two types of xylene isomerization catalysts. One type of isomerization catalyst can more or less equilibrate the four different $C_8$ aromatic compounds, including EB, to the concentrations dictated by thermodynamics under the reaction conditions. This allows maximum formation of PX from $C_8$ aromatics in a particular feed. Examples of these type catalysts include IFP/Engelhard Octafining™ and Octafining II™ catalysts used in the respective processes. Other types of xylene isomerization catalysts can effect EB conversion in addition to xylene isomerization, generally in the presence of hydrogen. As discussed earlier, these types of catalysts will remove EB and produce benzene and ethane as byproducts. This may be a desirable disposition of EB, depending on supplies and demands of various products as well as other equipment present in a particular plant. Examples include Mobil High Temperature Isomerization (MHTI™) catalysts, Mobil High Activity Isomerization catalysts (MHAI™), and UOP ISOMAR™ I-100 catalysts. For liquid-phase isomerization, the isomerization catalyst can more or less equilibrate the three xylene isomers to the concentrations dictated by thermodynamics under the reaction conditions with generally lower levels of EB conversion as described in WO 2011/133326, which is incorporated by reference herein.

A number of suitable isomerization reactors may be used for the present disclosure. Some non-limiting examples are described in U.S. Pat. Nos. 4,899,011 and 4,236,996.

For the present disclosure, a xylene isomerization reaction may be carried out in a liquid phase, a vapor (gas) phase, a super critical phase, or combinations thereof. The consumption of energy and the specific composition of the aromatic feed stream being isomerized will influence the isomerization reaction conditions and the physical state of the aromatic feed stream in the xylene isomerization reactor.

This invention is directed to a process for producing PX-rich product comprising: (1) separating a feedstock comprising $C_8^+$ aromatics to produce a $C_8$ aromatics-rich stream and a $C_9^+$ aromatics-rich stream; (2) separating at least a portion of said $C_8$ aromatics-rich stream to produce a PX-rich product stream and a PX-depleted raffinate stream; (3) isomerizing at least a portion of said PX-depleted raffinate stream to produce a first isomerate stream having a higher PX concentration than said PX-depleted raffinate stream; (4) isomerizing at least another portion of said PX-depleted raffinate stream to produce a second isomerate stream having a higher PX concentration than said PX-depleted raffinate stream; (5) separating $C_7^-$ hydrocarbons from at least a portion of said second isomerate stream and optionally at least a portion of said first isomerate stream to produce a $C_7^-$ hydrocarbons-rich stream and a $C_7^-$ hydrocarbons-depleted isomerate stream having a lower $C_7^-$ hydrocarbons concentration than said second and optionally said first isomerate streams; (6) separating at least a portion of said first isomerate stream and optionally at least a portion of said $C_7^-$ hydrocarbons-depleted isomerate stream to produce a PX-rich effluent stream and a PX-depleted effluent stream; (7) supplying a least a portion of said PX-depleted effluent stream to isomerizing step (3) and/or (4); (8) recycling at least a portion of said PX-rich effluent stream to separating step (1) and, optionally, separating step (2); and (9) recovering at least a portion of said PX-rich product stream as said PX-rich product. Optionally, the $C_9^+$-aromatics-rich stream may be separated downstream of separating (1), such as by fractionation, to produce an OX-rich steam and an OX-depleted $C_9^+$ stream. In embodiments, said process comprises isomerizing at least partially in the liquid phase in said isomerizing (4) to produce said second isomerized stream having a higher PX concentration than said PX-depleted raffinate stream.

In embodiments, said process comprises separating at least partially in the liquid phase in said separating step (6) to produce said PX-rich effluent stream and said PX-depleted effluent stream.

In embodiments, said process comprises isomerizing at least partially in the liquid phase in said isomerizing step (3) to produce said first isomerate stream having a higher PX concentration than said PX-depleted raffinate stream, and preferably higher than said PX-depleted effluent stream.

In embodiments, said process comprises isomerizing at least partially in the vapor phase in said isomerizing step (4) to produce said second isomerate stream having a higher PX concentration than said PX-depleted raffinate stream.

In embodiments, said two parallel isomerization systems comprise a liquid-phase reaction system and a vapor-phase isomerization system, each of which comprises at least one of xylenes isomerization, EB dealkylation, and EB isomerization.

In embodiments, said process comprises processing at least a portion of said PX-rich effluent stream in a benzene removal system to produce a benzene-rich stream and a benzene-depleted, PX-rich effluent stream; and recycling said benzene-depleted, PX-rich stream to said separating step (1) and/or said separating step (2).

In embodiments, said separating step (1) and said separating step (5) each comprises at least one distillation column.

The invention is also directed to a process for producing a PX-rich product comprising: (a) separating a feedstock comprising $C_8^+$ aromatics to produce a $C_8$ aromatics-rich stream and a $C_9^+$ aromatics-rich stream; (b) separating at least a portion of said $C_8$ aromatics-rich stream to produce a PX-rich effluent stream and a PX-depleted effluent stream; (c) separating said PX-rich effluent stream to produce a PX-rich product stream having a higher PX concentration than said PX-rich effluent stream and a PX-depleted raffinate stream; (d) isomerizing at least a portion of said PX-depleted effluent stream and at least a portion of said PX-depleted raffinate stream to produce a first isomerate stream having a higher PX concentration than said PX-depleted effluent and said PX-depleted raffinate streams; (e) isomerizing at least another portion of said PX-depleted raffinate stream to produce a second isomerate stream having a higher PX concentration than said PX-depleted raffinate stream (f) separating $C_7^-$ hydrocarbons from at least a portion of said second isomerate stream and optionally at least a portion of said first isomerate stream to produce a $C_7^-$ hydrocarbons-rich stream and a $C_7^-$ hydrocarbons-depleted isomerate stream having a lower $C_7^-$ hydrocarbons concentration than said second and, optionally, said first isomerate streams; (g) recycling at least a portion of at least one of said first isomerate stream and said $C_7^-$ hydrocarbons-depleted isomerate stream to said separating (a); and (h) recovering at least a portion of said PX-rich product stream as said PX-rich product. Optionally, the $C_9^+$-aromatics-rich stream may then be separated downstream of separating (a), such as by fractionation, to produce an OX-rich steam and an OX-depleted $C_9^+$ stream.

In embodiments, said process comprises separating at least partially in the liquid phase in said separating step (b) to produce said PX-rich effluent stream and said PX-depleted effluent stream.

In embodiments, said process comprises isomerizing at least partially in the liquid phase in said isomerizing step (d) to produce said first isomerate stream having a higher PX concentration than said PX-depleted raffinate and said PX-depleted effluent streams.

In embodiments, said process comprises isomerizing at least partially in the vapor phase in said isomerizing step (e) to produce said second isomerate stream having a higher PX concentration than said PX-depleted raffinate stream.

In embodiments, said two parallel isomerization systems comprise a liquid-phase reaction system and a vapor-phase isomerization system, each of which comprises at least one of xylenes isomerization, EB dealkylation, and EB isomerization.

In embodiments, said process comprises processing at least a portion of said first isomerate stream in a benzene removal system to produce a benzene-rich stream and a benzene-depleted stream, and recycling said benzene-depleted stream to said separating step (a) and/or said separating step (b).

In embodiments, said separating step (a) and said separating step (f) each comprises at least one distillation column.

It is an object of the invention to significantly reduce the energy required to produce PX and, optionally, OX by minimizing the amount of xylenes recycle and minimizing the energy-intensive vapor-phase isomerization.

It is yet another object of the invention to significantly increase the plant output for PX and, optionally, OX productions by utilizing the additional capacity created through minimizing recycle and bypassing at least a portion of the vapor-phase isomerization, preferably bypassing all of the vapor-phase isomerization.

Figure 2:
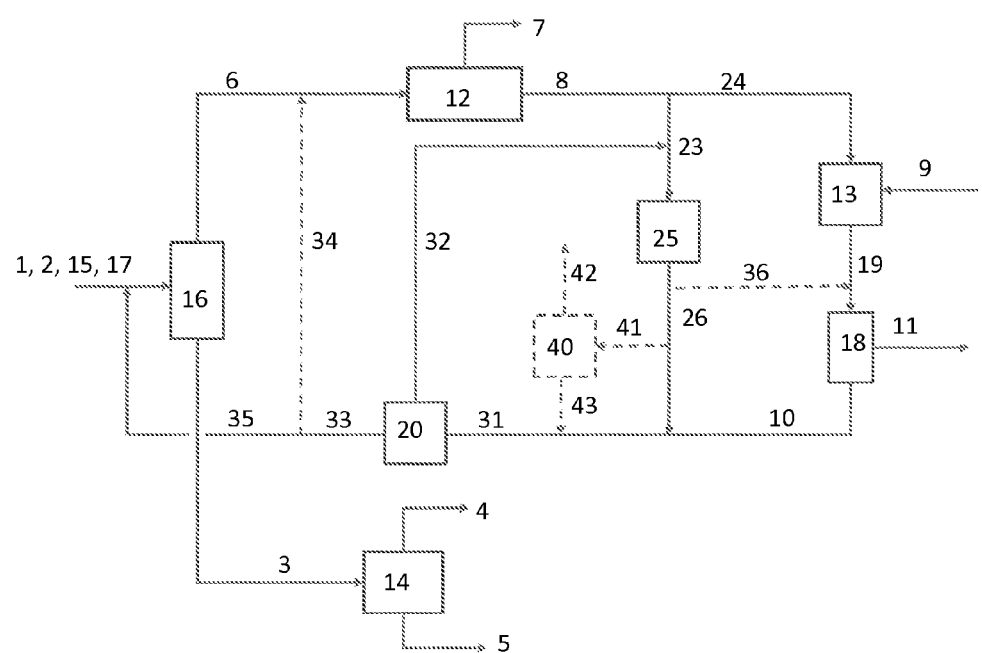
FIG. 2 is a schematic illustrating an embodiment of the invention.

The invention will be better understood by reference to FIG. 2, which illustrates a specific embodiment of the invention. As shown in FIG. 2, various feed sources comprising $C_8^+$ aromatics, such as 1, 2, 15, and 17, as described above, are sent to fractionator 16, which removes $C_9^+$ aromatics and, optionally, OX from the feed. The $C_8$ aromatics overhead is sent via line 6 to PX recovery 12, which may be provided by a crystallization unit or selective adsorption unit both of which are known in the art (such as a Parex™ unit). PX-rich product is taken off in line 7 and PX-depleted raffinate 8, comprising mostly other non-PX $C_8$ aromatics, is split and sent in parallel to vapor-phase xylenes isomerization 13, having a source of hydrogen 9, and liquid-phase xylenes isomerization 25 via lines 24 and 23, respectively. The liquid-phase xylenes isomerization 25 generates first isomerate (or isomerization product) 26 having a near-equilibrium concentration of xylene isomers. The vapor-phase xylenes isomerization 13 generates second isomerate 19 having a near-equilibrium concentration of xylene isomers. The second isomerate 19 passes to detoluenization fractionation 18, which removes $C_7^-$ hydrocarbons in stream 11 to yield $C_7^-$ depleted isomerate stream 10.

Although WO 2012/058106 and WO 2012/058108 have shown that splitting the PX-depleted raffinate stream 8 into streams 23 and 24 can reduce energy consumption by moving streams away from the vapor phase xylene isomerization 13, which is more energy intensive than liquid-phase isomerization 25, the splitting does not reduce the quantity of xylenes recycle.

This invention unexpectedly discovered that raising the PX concentrations in first isomerate 26 and $C_7^-$ depleted isomerate 10 can reduce xylenes recycle and achieve more energy savings and/or capacity increases. This can be done by processing the isomerates in xylenes separator 20 via line 31. The xylenes separator 20 generates a PX-rich effluent stream 33, which is recycled to fractionator 16 via line 35 and, optionally, to PX recovery 12 via line 34, and a PX-depleted effluent stream 32 of mostly non-PX C8 aromatics, which is recycled to liquid-phase isomerization 25. Optionally, at least a portion of first isomerate 26 may be sent to detoluenization fractionation 18 via line 36 to remove $C_7^-$ hydrocarbons. Optionally, the bottoms product 3 from fractionator 16 may be advantageously fractionated in 14 to yield an overheads product 4 of OX and bottoms product 5 of $C_9^+$ aromatic hydrocarbons.

FIG. 2 also shows that optionally at least a portion of first isomerate 26 from liquid-phase isomerization 25 can be sent to one or more locations such as benzene removal 40 via line 41 and detoluenization fractionation 18 via line 36. The amount sent to each location is determined by the need to remove $C_9^+$, benzene, and other $C_7^-$ byproducts. The byproducts from vapor-phase xylenes isomerization 13 and liquid-phase xylenes isomerization 25 may need to be removed to prevent buildup and/or to be acceptable for PX recovery 12, especially if selective adsorption is used for recovering PX. The $C_9^+$ aromatics can be removed in fractionator 16 or in one or more devices that employ separation techniques such as membrane, extraction, and adsorption. Similarly, benzene can be removed in 40 to generate a benzene-rich stream 42 and a benzene-depleted stream 43 using one or more devices that employ separation techniques such as distillation, extraction, membrane, and adsorption. The benzene-depleted stream 43 may be sent to xylenes separator 20.

Figure 3:
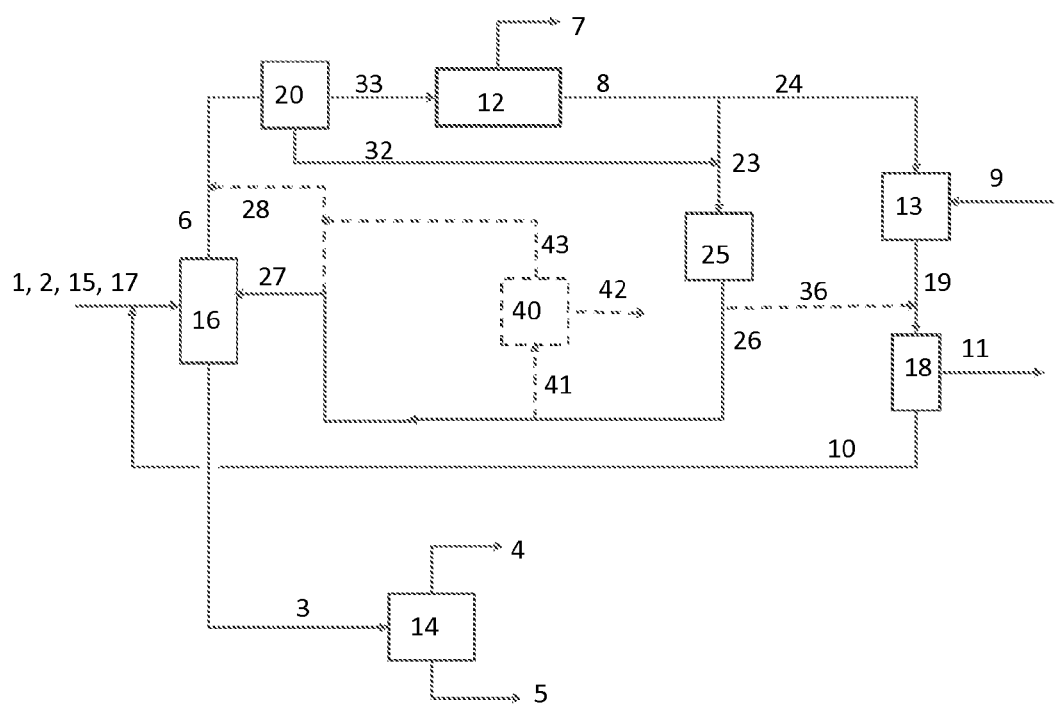
FIG. 3 is a schematic illustrating an additional embodiment of the invention.

FIG. 3 shows another embodiment of the invention. As shown in FIG. 3, various feed sources comprising $C_8^+$ aromatics, such as 1, 2, 15, and 17, as described above, are sent to fractionator 16, which removes $C_9^+$ aromatics and, optionally, OX from the feed. The $C_8$ aromatics overhead is sent via line 6 to xylenes separator 20, which generates PX-rich effluent stream 33 and PX-depleted effluent stream 32 comprising mostly MX, OX, and EB. The PX-depleted effluent 32 is sent to liquid-phase xylenes isomerization 25. The PX-rich effluent stream 33 is sent to PX recovery 12, which produces PX-rich product 7 and PX-depleted raffinate stream 8 comprising a majority of $C_8$ aromatics other than PX. A portion of PX-depleted raffinate 8 is sent to liquid-phase xylenes isomerization 25 via line 23. The liquid-phase xylenes isomerization 25 generates a first isomerate (or isomerization product) 26 having a near-equilibrium concentration of xylene isomers, which is recycled to fractionator 16 via line 27 and/or to xylenes separator 20 via line 28. The remainder of PX-depleted raffinate 8 is sent via line 24 to vapor-phase xylenes isomerization 13, which has a source of hydrogen 9, to generate a second isomerate 19 having a near-equilibrium concentration of xylene isomers. The second isomerate 19 passes to detoluenization fractionation 18 which removes $C_7^-$ in stream 11 to yield $C_7^-$ depleted isomerate stream 10 which is processed in fractionator 16. Optionally, the bottoms product 3 from fractionator 16 may be advantageously fractionated in 14 to yield an overheads product 4 of OX and bottoms product 5 of $C_9^+$ aromatic hydrocarbons.

FIG. 3 also shows that the first isomerate 26 from the liquid-phase isomerate 25 may be optionally sent to one or more locations such as fractionator 16 via line 27, benzene removal 40 via line 41, detoluenization fractionation 18 via line 36, and xylenes separator 20 via line 28. The amount sent to each location is determined by the need to remove byproducts which include $C_9^+$ aromatics, benzene, and other $C_7^-$ hydrocarbons. The byproducts from vapor-phase isomerization 13 and liquid-phase xylenes isomerization 20 may need to be removed to prevent buildup and/or to be acceptable for PX recovery 12, especially if selective adsorption is used for recovering PX. The $C_9^+$ aromatics can be removed in fractionator 16 or in one or more devices that employ separation techniques such as membrane, extraction, and adsorption. Similarly, benzene can be removed in 40 to generate a benzene-rich stream 42 and a benzene depleted stream 43 using one or more devices that employ separation techniques such as distillation, extraction, membrane, and adsorption. Optionally, at least a portion of the benzene-depleted stream can be sent to xylenes separator 20 via line 43 and/or fractionator 16 via line 44 (not shown in FIG. 3). Optionally, the $C_9^+$ aromatics and benzene can be removed simultaneously using one or more devices that employ separation techniques such as distillation, extraction, membrane, and adsorption.

While the embodiments disclosed in FIGS. 2 and 3 describe the coupling of two in-series xylenes separation systems with two parallel xylenes isomerization systems and the related fractionation facilities, it will be understood by one of ordinary skill in the art that FIGS. 2 and 3 are merely representative of the present invention and that many variations thereof can be readily envisioned.

In another embodiment this invention relates to:

1. A process for producing a para-xylene-rich product, the process comprising:
   (a) separating a feedstock comprising $C_8^+$ aromatics to produce a $C_8$ aromatics-rich stream and a $C_9^+$ aromatics-rich stream;
   (b) separating at least a portion of said $C_8$ aromatics-rich stream to produce a para-xylene-rich product stream and a para-xylene-depleted raffinate stream;
   (c) isomerizing at least a portion of said para-xylene-depleted raffinate stream to produce a first isomerate stream having a higher para-xylene concentration than said para-xylene-depleted raffinate stream;
   (d) isomerizing at least another portion of said para-xylene-depleted raffinate stream to produce a second isomerate stream having a higher para-xylene concentration than said para-xylene-depleted raffinate stream;
   (e) separating $C_7^-$ hydrocarbons from at least a portion of said second isomerate stream and optionally at least a portion of said first isomerate stream to produce a $C_7^-$ hydrocarbons-rich stream and a $C_7^-$ hydrocarbons-depleted isomerate stream having a lower $C_7^-$ hydrocarbons concentration than said second and, optionally, said first isomerate streams;
   (f) separating (preferably with a xylenes separating system) at least a portion of said first isomerate stream and optionally at least a portion of said $C_7^-$ hydrocarbons-depleted isomerate stream to produce a para-xylene-rich effluent stream and a para-xylene-depleted effluent stream;
   (g) supplying a least a portion of said para-xylene-depleted effluent stream to isomerizing step (c) and/or step (d);
   (h) recycling at least a portion of said para-xylene-rich effluent stream to separating step (a); and, optionally, separating step (b); and
   (i) recovering at least a portion of said para-xylene-rich product stream as said para-xylene-rich product.

2. The process of paragraph 1, wherein said para-xylene-rich product stream comprises at least 90 wt % para-xylene based on the total weight of said para-xylene-rich product stream.

3. The process of paragraph 1 or 2, wherein said para-xylene-rich effluent stream comprises at least 30 wt % para-xylene based on the total weight of xylenes in said para-xylene-rich effluent stream.

4. The process of any of the preceding paragraphs, wherein said separating (a) comprises distillation of said feedstock.

5. The process of any of the preceding paragraphs, wherein said separating (b) and separating (f) each comprises at least one of selective adsorption, selective crystallization, selective extraction, and selective membrane separation.

6. The process of any of paragraphs 1 to 4, wherein said separating (f) is carried out in a separation system operated at least partially in liquid phase under conditions sufficient to generate said para-xylene-rich effluent stream and said PX-depleted effluent stream.

7. The process of any of the preceding paragraphs, wherein said isomerizing (c) is carried out in an isomerization system containing at least one catalyst operated at least partially in liquid phase under conditions sufficient to isomerize meta-xylene and/or ortho-xylene to para-xylene and/or to convert ethylbenzene to benzene and/or xylenes.

7. The process of any of the preceding paragraphs, wherein said isomerizing (d) is carried out in an isomerization system containing at least one catalyst operated at least partially in vapor phase under conditions sufficient to isomerize meta-xylene and/or ortho-xylene to para-xylene and/or to convert ethylbenzene to benzene and/or xylenes.

9. The process of any of the preceding paragraphs further comprising separating benzene from at least a portion of said first isomerate stream in a benzene removal system to produce a benzene-rich stream and a benzene-depleted stream.

10. The process of paragraph 9 further comprising sending at least a portion of said benzene-depleted stream to said separating step (a).

11. The process of any of the preceding paragraphs, wherein said separating (e) comprises distillation of said isomerate stream(s).

12. The process of any of the preceding paragraphs further comprising separating said $C_9^+$-aromatics-rich stream in an ortho-xylene-recovery system to produce an ortho-xylene-rich stream and an OX-depleted $C_9^+$-aromatics stream.

13. The process of any of the preceding paragraphs, wherein said feed comprising $C_8^+$ aromatics includes at least one feed selected from the group consisting of a $C_8^+$ selective toluene disproportionation product, a $C_8^+$ transalkylation product, a $C_8^+$ reformate product, a $C_8^+$ toluene disproportionation product, and a $C_8^+$ toluene methylation product, and a $C_8^+$ benzene methylation product.

14. A process for producing a para-xylene-rich product, the process comprising:
  (a) separating a feedstock comprising $C_8^+$ aromatics to produce a $C_8$ aromatics-rich stream and a $C_9^+$ aromatics-rich stream;
  (b) separating at least a portion of said $C_8$ aromatics-rich stream to produce a para-xylene-rich effluent stream and a para-xylene-depleted effluent stream;
  (c) separating said para-xylene-rich effluent stream to produce a para-xylene-rich product stream having a higher para-xylene concentration than said para-xylene-rich effluent stream and a para-xylene-depleted raffinate stream;
  (d) isomerizing at least a portion of said para-xylene-depleted effluent stream and at least a portion of said para-xylene-depleted raffinate stream to produce a first isomerate stream having a higher para-xylene concentration than said para-xylene-depleted effluent and said para-xylene-depleted raffinate streams;
  (e) isomerizing at least another portion of said para-xylene-depleted raffinate stream to produce a second isomerate stream having a higher para-xylene concentration than said para-xylene-depleted raffinate streams;
  (f) separating $C_7^-$ hydrocarbons from at least a portion of said second isomerate stream and optionally at least a portion of said first isomerate stream to produce a $C_7^-$ hydrocarbons-rich stream and a $C_7^-$ hydrocarbons-depleted isomerate stream having a lower $C_7^-$ hydrocarbons concentration than said second and optionally said first isomerate streams;
  (g) recycling at least a portion of at least one of said first isomerate stream and said $C_7^-$ hydrocarbons-depleted isomerate stream to said separating step (a); and
  (h) recovering at least a portion of said para-xylene-rich product stream as said para-xylene-rich product.

15. The process of paragraph 4, wherein said para-xylene-rich effluent stream comprises at least 30 wt % para-xylene based on the total amount of xylenes in said para-xylene-rich effluent stream.

16. The process of paragraph 4 or 15, wherein said para-xylene-rich product stream comprises at least 90 wt % para-xylene based on the total weight of said para-xylene-rich product stream.

17. The process of any of paragraphs 14 to 16, wherein said separating step (a) comprises distillation of said feedstock.

18. The process of any of paragraphs 14 to 17, wherein said separating step (b) and separating step (c) each comprises at least one of selective adsorption, selective crystallization, selective extraction, and selective membrane separation.

19. The process of any of paragraphs 14 to 17, wherein said separating step (b) is carried out in a separation system operated at least partially in liquid phase under conditions sufficient to generate said para-xylene-rich effluent stream and said PX-depleted effluent stream.

20. The process of any of paragraphs 14 to 19, wherein said isomerizing step (d) is carried out in an isomerization system containing at least one catalyst operated at least partially in liquid phase under conditions sufficient to isomerize meta-xylene and/or ortho-xylene to para-xylene and/or to convert ethylbenzene to benzene and/or xylenes.

21. The process of any of paragraphs 14 to 20, wherein said isomerizing step (e) is carried out in an isomerization system containing at least one catalyst operated at least partially in vapor phase under conditions sufficient to isomerize meta-xylene and/or ortho-xylene to para-xylene and/or to convert ethylbenzene to benzene and/or xylenes.

22. The process of any of paragraphs 14 to 21 further comprising separating benzene from at least a portion of said first isomerate stream in a benzene removal system to produce a benzene-rich stream and a benzene-depleted stream.

23. The process of paragraph 22 further comprising sending at least a portion of said benzene-depleted stream to said separating step (a).

24. The process of any of paragraphs 14 to 23, wherein said separating step (f) comprises distillation of said isomerate stream(s).

25. The process of any of paragraphs 14 to 24 further comprising separating said $C_9^+$-aromatics-rich stream in an ortho-xylene-recovery system to produce an ortho-xylene-rich stream and an ortho-xylene-depleted $C_9^+$-aromatics stream.

26. The process of any of paragraphs 14 to 25, wherein said feed comprising $C_8^+$ aromatics includes at least one feed selected from the group consisting of a $C_8^+$ selective toluene disproportionation product, a $C_8^+$ transalkylation product, a $C_8^+$ reformate product, a $C_8^+$ toluene disproportionation product, and a $C_8^+$ toluene methylation product, and a $C_8^+$ benzene methylation product.

27. The process of any of paragraphs 1 to 13, wherein said separating (f) is carried out in a separation system operated at least partially in liquid phase under conditions sufficient to generate said para-xylene-rich effluent stream and said PX-depleted effluent stream; the isomerizing (c) is carried out in an isomerization system containing at least one catalyst operated at least partially in liquid phase under conditions sufficient to isomerize meta-xylene and/or ortho-xylene to para-xylene and/or to convert ethylbenzene to benzene and/or xylenes; and said isomerizing (d) is carried out in an isomerization system containing at least one catalyst operated at least partially in vapor phase under conditions sufficient to isomerize meta-xylene and/or ortho-xylene to para-xylene and/or to convert ethylbenzene to benzene and/or xylenes.

EXAMPLES

Computer simulations using the PROII™ program, commercially available, were conducted to verify the benefits of the present invention. Certain assumptions were made, including: (a) the isomerization unit isomerizes PX, MX, and OX to their thermodynamic equilibrium; (b) the equilibrium PX concentration in xylenes (excluding EB) is 24%;

and (c) the isomerization unit converts EB to benzene, toluene, xylenes, or other hydrocarbons. Examples 1 and 2 illustrate the benefits of the embodiments of the present invention shown in FIGS. 2 and 3, respectively, in comparison to the conventional process shown in FIG. 1.

Example 1

This example compares the production of PX using the embodiment of the present invention shown in FIG. 2 to that using a conventional process shown in FIG. 1. The PROII simulation was based on the following assumptions.
 The PX production rate was kept at 800 thousand tons per year for both simulations.
 The fresh feed to said fractionator 16 had a composition of 1.03 mol % toluene, 6.48 mol % EB, 10.16 mol % PX, 24.26 mol % MX, 13.09 mol % OX, and 43.62 mol % A9+, and 1.36 mol % non-aromatics.
 Said PX recovery 12 was a selective adsorption unit producing said PX-rich product stream having a PX concentration of 99.7 wt. %.
 Said PX-depleted raffinate stream 8 was equally split between said liquid-phase isomerization 25 and said vapor-phase isomerization 13.
 Said benzene removal 40 and said line 36 to detoluenization fractionation 18 were not included in simulation.
 Three cases were studied in which the PX concentration in said PX-rich effluent stream 33 was assumed to be 30 wt %, 40 wt %, and 50 wt % based on the total weight of xylenes in the stream, respectively.
 The energy consumption related to said xylenes separator 20 was not considered.

The simulation results are shown in Table 1. It is seen that the embodiment shown in FIG. 2 could achieve significant energy savings in the range of 22.8 to 60.6 mega Watts over the conventional process. In addition to the energy savings, the embodiment also reduced feed rate by 7.4 to 20.4 kilo-tons per year. Other benefits (not shown in Table 1) include PX production capacity increases for existing plants and investments reduction for new plants.

Example 2

This example compares the production of PX using the embodiment of the present invention shown in FIG. 3 to that using a conventional process shown in FIG. 1. The PROII simulation was based on the same assumptions as in Example 1.

The simulation results are shown in Table 2. It is seen that the embodiment shown in FIG. 3 could achieve significant energy savings in the range of 40.4 to 83.2 mega Watts over the conventional process. In addition to the energy savings, the embodiment also reduced feed rate by 11.7 to 26.8 kilo-tons per year. Other benefits (not shown in Table 2) include PX production capacity increases for existing plants and investments reduction for new plants.

TABLE 1

Benefits from the Embodiment of the Invention Shown in FIG. 2

| | PX-concentration in the second PX-rich stream (wt %) | | |
| --- | --- | --- | --- |
| | 30 | 40 | 50 |
| Energy Savings (MW) | 22.8 | 46.3 | 60.6 |
| Reduction of feed rate (kta) | 7.4 | 15.5 | 20.4 |

TABLE 2

Benefits from the Embodiment of the Invention Shown in FIG. 3

| | PX-concentration in the first PX-rich stream (wt %) | | |
| --- | --- | --- | --- |
| | 30 | 40 | 50 |
| Energy Savings (MW) | 40.4 | 71.8 | 83.2 |
| Reduction of feed rate (kta) | 11.7 | 22.1 | 26.8 |

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of "consisting of," or "is" preceding the recitation of the composition, element, or elements and vice versa. Thus, the term "comprising" encompasses the terms "consisting essentially of," "is," and "consisting of" and anyplace "comprising" is used "consisting essentially of," "is," or "consisting of" may be substituted therefor.

What is claimed is:
1. A process for producing a para-xylene-rich product, the process comprising:
 (a) separating a feedstock comprising C8+ aromatics to produce a C8 aromatics-rich stream and a C9+ aromatics-rich stream;
 (b) separating at least a portion of said C8 aromatics-rich stream to produce a para-xylene-rich effluent stream and a para-xylene-depleted effluent stream;
 (c) separating said para-xylene-rich effluent stream to produce a para-xylene-rich product stream having a higher para-xylene concentration than said para-xylene-rich effluent stream and a para-xylene-depleted raffinate stream;
 (d) isomerizing at least a portion of said para-xylene-depleted effluent stream and at least a portion of said para-xylene-depleted raffinate stream to produce a first isomerate stream having a higher para-xylene concentration than said para-xylene-depleted effluent and said para-xylene-depleted raffinate streams;
 (e) isomerizing at least another portion of said para-xylene-depleted raffinate stream to produce a second isomerate stream having a higher para-xylene concentration than said para-xylene-depleted raffinate streams;
 (f) separating C7− hydrocarbons from at least a portion of said second isomerate stream and optionally at least a portion of said first isomerate stream to produce a C7− hydrocarbons-rich stream and a C7− hydrocarbons-depleted isomerate stream having a lower C7− hydrocarbons concentration than said second and optionally said first isomerate streams;

(g) recycling at least a portion of at least one of said first isomerate stream and said C7− hydrocarbons-depleted isomerate stream to said separating step (a); and (h) recovering at least a portion of said para-xylene-rich product stream as said para-xylene-rich product.

2. The process of claim 1, wherein said para-xylene-rich effluent stream comprises at least 30 wt % para-xylene based on the total amount of xylenes in said para-xylene-rich effluent stream.

3. The process of claim 1, wherein said para-xylene-rich product stream comprises at least 90 wt % para-xylene based on the total weight of said para-xylene-rich product stream.

4. The process of claim 1, wherein said separating step (a) comprises distillation of said feedstock.

5. The process of claim 1, wherein said separating step (b) and separating step (c) each comprises at least one of selective adsorption, selective crystallization, selective extraction, and selective membrane separation.

6. The process of claim 1, wherein said separating step (b) is carried out in a separation system operated at least partially in liquid phase under conditions sufficient to generate said para-xylene-rich effluent stream and said PX-depleted effluent stream.

7. The process of claim 1, wherein said isomerizing step (d) is carried out in an isomerization system containing at least one catalyst operated at least partially in liquid phase under conditions sufficient to isomerize meta-xylene and/or ortho-xylene to para-xylene and/or to convert ethylbenzene to benzene and/or xylenes.

8. The process of claim 1, wherein said isomerizing step (e) is carried out in an isomerization system containing at least one catalyst operated at least partially in vapor phase under conditions sufficient to isomerize meta-xylene and/or ortho-xylene to para-xylene and/or to convert ethylbenzene to benzene and/or xylenes.

9. The process of claim 1 further comprising separating benzene from at least a portion of said first isomerate stream in a benzene removal system to produce a benzene-rich stream and a benzene-depleted stream.

10. The process of claim 9 further comprising sending at least a portion of said benzene-depleted stream to said separating step (a).

11. The process of claim 1, wherein said separating step (f) comprises distillation of said isomerate stream(s).

12. The process of claim 1 further comprising separating said C9+-aromatics-rich stream in an ortho-xylene-recovery system to produce an ortho-xylene-rich stream and an ortho-xylene-depleted C9+-aromatics stream.

13. The process of claim 1, wherein said feed comprising C8+ aromatics includes at least one feed selected from the group consisting of a C8+ selective toluene disproportionation product, a C8+ transalkylation product, a C8+ reformate product, a C8+ toluene disproportionation product, and a C8+ toluene methylation product, and a C8+ benzene methylation product.

* * * * *